United States Patent
Leung et al.

(10) Patent No.: US 12,252,681 B2
(45) Date of Patent: Mar. 18, 2025

(54) SYSTEMS, DEVICES, AND METHODS FOR STERILIZING BIOREACTORS AND CULTURE MEDIA

(71) Applicant: Upside Foods, Inc., Berkeley, CA (US)

(72) Inventors: Matthew Leung, Richmond, CA (US); Patricia Rae Benton, Huntington Beach, CA (US); Cameron Gentry Copeland, Walnut Creek, CA (US); Stephen K. Hsu, Albany, NY (US); Kalle Lukyan Johnson, Orinda, CA (US)

(73) Assignee: Upside Foods, Inc., Berkeley, CA (US)

( * ) Notice: Subject to any disclaimer, the term of this patent is extended or adjusted under 35 U.S.C. 154(b) by 951 days.

(21) Appl. No.: 16/996,567

(22) Filed: Aug. 18, 2020

(65) Prior Publication Data

US 2022/0056394 A1    Feb. 24, 2022

(51) Int. Cl.
| | |
|---|---|
| *A61L 2/20* | (2006.01) |
| *A61L 2/00* | (2006.01) |
| *C12M 1/00* | (2006.01) |
| *C12M 1/12* | (2006.01) |
| *C12M 1/34* | (2006.01) |
| *C12M 3/04* | (2006.01) |

(52) U.S. Cl.
CPC .......... *C12M 37/00* (2013.01); *A61L 2/0094* (2013.01); *A61L 2/20* (2013.01); *C12M 23/22* (2013.01); *C12M 27/10* (2013.01); *C12M 39/00* (2013.01); *C12M 41/44* (2013.01)

(58) Field of Classification Search
CPC ........ A61L 2/0094; A61L 2/20; C12M 37/00; C12M 39/00
See application file for complete search history.

(56) References Cited

U.S. PATENT DOCUMENTS

| | | | |
|---|---|---|---|
| 6,686,194 B1 | 2/2004 | Mutzel et al. | |
| 2007/0095854 A1* | 5/2007 | House ................... | B01L 3/0293 222/63 |
| 2008/0261308 A1* | 10/2008 | Fike ......................... | C12N 1/00 435/404 |
| 2009/0142226 A1* | 6/2009 | McWhorter .............. | A61L 2/20 424/661 |
| 2010/0310418 A1* | 12/2010 | Mason ...................... | A61L 2/20 422/37 |
| 2013/0130361 A1* | 5/2013 | Okano ................... | C12M 37/00 137/15.01 |
| 2017/0253849 A1 | 9/2017 | Miller | |

OTHER PUBLICATIONS

International Search Report and Written Opinion as received in PCT Application No. PCT/US2021/045585 dated Dec. 3, 2021.

* cited by examiner

*Primary Examiner* — Timothy C Cleveland
(74) *Attorney, Agent, or Firm* — Keller Preece PLLC

(57) ABSTRACT

Disclosed herein are systems, devices, and methods for sterilization. In some variations, a method of sterilizing a bioreactor system may comprise circulating a sterilant in a bioreactor and an enclosed vessel in fluidic communication with the bioreactor. The enclosed vessel may comprise cell culture media. The sterilant may be circulated for a dwell time sufficient to sterilize at least one of the bioreactor, the vessel, and the cell culture media.

20 Claims, 10 Drawing Sheets

| | Chlorine Dioxide Gas | Vapor Phase Hydrogen Peroxide | Ozone Gas | Peroxide Peracetic Acid Fogging | Ethylene Oxide Gas | Nitrogen Dioxide Gas (dinitrogen tetraoxide) |
|---|---|---|---|---|---|---|
| Volumes of area to be sterilized | Very large | Small | Small | Very Small | Small | Undetermined |
| Shape of the area being sterilized | No effect | Poor Diffusion into areas not in line of sight with the generator | Inactivated before it reached all areas of some shapes | Poor Diffusion | No effect | No effect |
| Shadow Areas such as equipment in the area being sterilized | No effect | Equipment can act as barriers | Some issues | Poor diffusion around equipment | No effect | No effect |
| Temperature | Above 11C | Above 109C | ~60C | 18C-30C | 37C – 60C | 10C – 30C |
| Relative Humidity | 60-75% | >85% | 80% | >85% | 40-80% | 80% |
| Wet surfaces | Yes | Yes | Yes/No | Yes/No | Yes | Yes/No |
| Injection rate | Static | Affected by shape of the area being sterilized | Affected by shape of the area being sterilized | Affected by shape of the area being sterilized | Static | Static |
| EPA Registration as a Sterilant | Yes | Yes | Purpose dependent | Formulation dependent | Formulation dependent | Unknown |
| Diffusion/Distribution | Very Good | Poor | Poor | Poor | Good | Very Good |
| Penetration | Very Good | Very Poor | Poor | Poor | Good | Very Good |
| Concentration Monitoring | Yes | Yes | Yes | No | Yes | Yes |
| GRAS | Yes (meat and poultry) | Yes (meat and poultry) | Yes (meat and poultry) | No | No | No |
| Safety profile | Good | Good | Good | Poor | Very Poor | Good |
| Material Compatibility | Low oxidation potential (0.95V) | Moderate Oxidation potential (1.78V) | High oxidation potential (2.05V) | High oxidation potential (1.81V) | Formulation dependent | Not an oxidant. known incompatible compounds include polyurethane nylon, Delrin, Cellulose, Copper |
| Explosive capability | 10% in air | Low potential | Highly explosive at high temp | 15% peracetic acid | 3% in Air, up to 12% in hydrocarbons. 7% in CO2 | Not explosive |
| Environmental safety | Very Good | Good | Good | Poor | Very Poor | |
| Toxicity | moderate | Low | moderate | High | Very High | No |
| Carcinogenicity | No | No | No | Yes | Very Carcinogenic | No |

FIG. 2

SYSTEMS, DEVICES, AND METHODS FOR STERILIZING BIOREACTORS AND CULTURE MEDIA

BACKGROUND

Sterilization of a bioreactor system is commonly a time and resource-intensive process. For example, while steam sterilization (e.g., steam-in-place, autoclave) is approved by the Food and Drug Administration (FDA), a bioreactor may need to be designed to withstand the high temperatures and pressures generated by autoclave sterilization. Cell culture media and liquid media (e.g., purified water) used in bioreactor systems may also need to undergo sterilization since they are also subject to contamination. For example, hydrated cell culture media may conventionally be sterilized using a combination of high temperature short time (HTST) pasteurization to inactivate viruses, and filtration (e.g., through a 0.1 µm to 0.2 µm filter) to remove contaminants such as bacteria and yeast. However, the combination of these multiple sterilization modalities have drawbacks including, but not limited to, an increase in the physical size and number of components of a bioreactor system, an increase in the number of processes to sterilize the bioreactor system and cell culture media, an increase in sterilization times, and ongoing costs (e.g., energy, regulatory, maintenance, personnel) to perform these separate sterilization processes. As such, additional systems, devices, and methods for sterilizing bioreactors and culture media may be desirable.

SUMMARY

Described herein are systems, devices and methods for sterilizing one or more of a bioreactor and a culture medium. For example, the methods may be useful for large-scale bioreactor systems configured to grow commercial-scale quantities of comestible meat. In some variations, a method of sterilizing a bioreactor system may comprise circulating a sterilant (e.g., chlorine dioxide gas, fluid) in a bioreactor and an enclosed vessel (e.g., mixing vessel) in fluidic communication with the bioreactor where the enclosed vessel comprises cell culture media. The sterilant may be circulated for a dwell time sufficient to sterilize at least two of the bioreactor, the vessel, and the cell culture medium.

In some variations, the bioreactor may be a first bioreactor. The sterilant may be circulated from the first bioreactor to a second bioreactor in fluidic communication with the first bioreactor. In some variations, the sterilant may comprise one or more of chlorine dioxide gas, ethylene oxide gas, hydrogen peroxide vapor, and peracetic acid vapor. In some variations, the bioreactor may be configured to grow a comestible meat product. In some variations, the bioreactor may comprise a fluid and the sterilant may be circulated for the dwell time sufficient to sterilize the fluid. In some variations, the fluid may be agitated in the bioreactor while circulating the sterilant.

In some variations, the sterilant may be removed from the bioreactor and the enclosed vessel. In some variations, a sterilization notification may be generated after removing the sterilant. In some variations, an amount of the sterilant may be measured in the bioreactor system. In some variations, the sterilant may be neutralized. In some variations, one or more additives may be introduced into the bioreactor after removing the sterilant. In some variations, introducing the one or more additives may comprise introducing an amino acid. In some variations, introducing the one or more additives may comprise introducing one or more of an anti-foaming agent, a shear protectant, a protein, a nutrient mixture, mammalian cells, bacteria cells, yeast cells, or insect cells.

In some variations, the dwell time is at least about one minute. In some variations, the cell culture media may comprise dehydrated cell culture media. In some variations, the cell culture media may comprise liquid cell culture media. In some variations, the bioreactor may comprise one or more of a polymer, glass, or metal.

In some variations, the bioreactor may be operated in one or more modes comprising a batch mode, a fed batch mode, a perfusion mode, a semi-continuous mode, or a continuous mode.

In some variations, the bioreactor may be configured to grow one or more of mammalian, avian, aquatic animal, insect, yeast, or bacterial cells. In some variations, the bioreactor may be configured to grow cells in one or more of a suspension or adherent culture.

In some variations, the bioreactor may be configured to grow cells on one or more of a microcarrier substrate and encapsulated in a substrate. In some variations, the bioreactor may be configured to grow a cell-based product. In some variations, the bioreactor may be configured to grow a protein-based product.

Also described here are methods of preparing a cell culture media. A method of preparing cell culture media may comprise circulating a chlorine dioxide gas in an enclosed vessel comprising dehydrated cell culture media. The chlorine dioxide gas may be circulated for a dwell time sufficient to sterilize at least one of the dehydrated cell culture media and the enclosed vessel. A fluid may be introduced into the enclosed vessel to hydrate the cell culture media.

In some variations, the enclosed vessel may be a mixing vessel configured to mix the cell culture media. In some variations, introducing the fluid may comprise generating a vortex flow in the enclosed vessel. In some variations, circulating the chlorine dioxide gas may comprise introducing the chlorine dioxide gas into a headspace of the enclosed vessel.

In some variations, the enclosed vessel may be a bioreactor. In some variations, introducing the cell culture media into the bioreactor. In some variations, the fluid in the bioreactor may be agitated while circulating the sterilant gas.

In some variations, the enclosed vessel may be a bioreactor configured to grow a comestible meat product. In some variations, the cell culture media may be agitated or mixed. In some variations, the fluid may comprise water.

In some variations, the chlorine dioxide gas may be removed from the enclosed vessel. In some variations, a sterilization notification may be generated after removing the sterilant. In some variations, the one or more non-sterilant gases may be circulated in a headspace of the enclosed vessel. In some variations, an amount of the chlorine dioxide gas being removed from the enclosed vessel may be measured.

In some variations, the chlorine dioxide gas may be neutralized. In some variations, the dwell time may be at least about one minute. In some variations, the bioreactor may comprise one or more of a polymer, glass, or metal. In some variations, the cell culture media may comprise an incomplete composition configured to grow cells with an addition of at least one other composition. In some variations, the cell culture media may comprise a complete composition configured to grow cells by itself.

In some variations, the bioreactor may be operated in one or more modes comprising a batch mode, a fed batch mode, a perfusion mode, a semi-continuous mode, or a continuous mode. In some variations, the enclosed vessel may be configured to grow a cell-based product. In some variations, the enclosed vessel may be configured to grow a protein-based product. In some variations, the enclosed vessel may be configured to grow one or more of mammalian, avian, aquatic animal, insect, yeast, or bacterial cells.

In some variations, the enclosed vessel may be configured to grow cells in one or more of a suspension or adherent culture. In some variations, the enclosed vessel may be configured to grow cells on one or more of a microcarrier substrate and encapsulated in a substrate. Also described here are systems. In some variations, a system may comprise a bioreactor, a mixing vessel in fluidic communication with the bioreactor and comprising dehydrated cell culture media, and a controller coupled to one or more fluid pumps. The controller may be configured to generate a fluid pump signal to circulate a sterilant in the bioreactor and the mixing vessel for a dwell time sufficient to sterilize at least one of the dehydrated cell culture media, the bioreactor, and the mixing vessel.

In some variations, the sterilant may comprise at least one of chlorine dioxide gas, ozone gas, ethylene oxide gas, hydrogen peroxide vapor, and peracetic acid vapor. In some variations, the bioreactor may comprise a fluid. The controller may be configured to generate a second fluid pump signal to circulate the fluid from the bioreactor to the mixing vessel to hydrate the cell culture media. In some variations, the second fluid pump signal may be configured to circulate the fluid to generate a fluid vortex in the mixing vessel. In some variations, the controller may be configured to generate a third fluid pump signal to circulate a non-sterilant gas into the bioreactor and the mixing vessel to remove the sterilant from the bioreactor and the mixing vessel.

In some variations, the fluid may comprise water. In some variations, the bioreactor may be configured to grow a comestible meat product. In some variations, the bioreactor may comprise a transparent portion. In some variations, the bioreactor may comprise one or more of a polymer, glass, or metal.

In some variations, the bioreactor may comprise an agitator. In some variations, the controller may be coupled to the agitator. The controller may be configured to generate a first agitation signal to agitate the fluid in the bioreactor when the sterilant is circulated in the fluid. In some variations, the controller may be configured to generate a second agitation signal to agitate the cell culture media introduced into the bioreactor. In some variations, the dwell time may be at least about one minute. In some variations, the bioreactor may be configured to operate in at least one of a batch mode, a fed batch mode, a perfusion mode, a semi-continuous mode, or a continuous mode.

BRIEF DESCRIPTION OF THE DRAWINGS

FIG. 2 is a table of example sterilant properties.

DETAILED DESCRIPTION

Figure 1A:
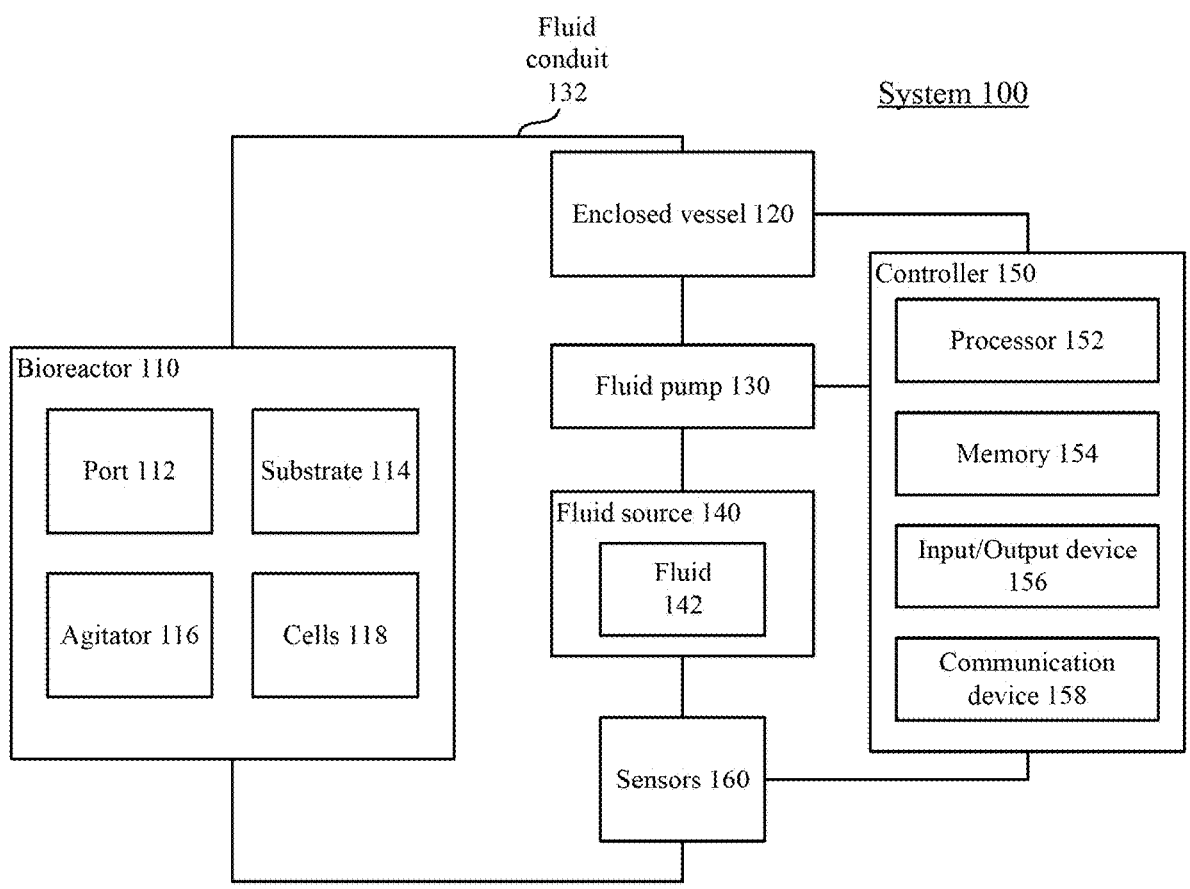
FIGS. 1A-1D are illustrative block diagrams of illustrative variations of a bioreactor system.

Described herein are systems, devices, and methods for sterilizing an enclosed vessel and/or cell culture media, and in particular, a bioreactor system used to grow a comestible meat product. For example, a bioreactor system may comprise a bioreactor, an enclosed vessel (e.g., mixing vessel, another bioreactor) in fluidic communication with the bioreactor, a fluid pump, a sterilant, and a controller configured to circulate the sterilant through the system for a dwell time sufficient to sterilize the system and compositions (e.g., cell culture media, fluid) disposed therein. The sterilant may dwell at sufficient dose and time to destroy one or more of viruses, bacteria, fungi, spores, and the like. In some variations, the sterilant may comprise a true gas configured to evenly circulate (e.g., flow, distribute) within an enclosed volume such as a bioreactor or vessel so as evenly sterilize (e.g., bioburden suppression, inactivate organisms) on all exposed surfaces and compositions disposed within the system. For example, the sterilant may comprise chlorine dioxide ($ClO_2$) gas or vapor, which is registered with the Environmental Protection Agency (EPA) as a sterilant. In some variations, the sterilant may comprise a vapor.

Also described here are methods of sterilizing one or more of a bioreactor, enclosed vessel, and components (e.g., substrate) and compositions (e.g., fluid, cell culture media, nutrients, additives) disposed therein. In some variations, a method of sterilizing a bioreactor system may comprise circulating a sterilant (e.g., sterilant gas) in a bioreactor and an enclosed vessel comprising cell culture media. The enclosed vessel may be in fluidic communication with the bioreactor. The sterilant may be circulated for a dwell time sufficient to sterilize the bioreactor and the vessel and cell culture medium. In some variations, a method of preparing cell culture media may additionally or alternatively comprise circulating chlorine dioxide gas in an enclosed vessel comprising dehydrated cell culture media. The chlorine dioxide gas may be circulated for a dwell time sufficient to sterilize the dehydrated cell culture media. A fluid may be introduced into the enclosed vessel to hydrate the sterilized cell culture media.

Accordingly, the systems, devices, and methods described herein may enable the reduction in size of a bioreactor and system, reduction in complexity of a sterilization process, reduction in energy usage, and an increase in sterilization efficiency with lower energy usage and costs. For example, a bioreactor undergoing gas sterilization need not have a pressure-rated design (e.g., thick, heavy, and expensive steel) configured to withstand the high pressures and temperatures associated with conventional steam sterilization. Therefore, one or more components of a bioreactor system (e.g., housing, substrate) may be composed at least partially of lighter and/or more cost-effective materials such as polymer and glass.

Additionally or alternatively, one or more components of a bioreactor system (e.g., scaffold) may be composed of temperature and/or pressure sensitive materials otherwise unsuitable for conventional sterilization methods. This may allow for more components to be sterilized together. For example, one or more compositions (e.g., cell culture media, fluid, nutrients, additives) may be sterilized within and at the same time as the bioreactor system, thereby simplifying a sterilization workflow without including HTST pasteurization or a sterilization filter.

Additionally, the sterilization methods described herein may be efficiently scaled for large-scale bioreactor systems (e.g., comprising a plurality of bioreactors and other vessels) without significant additional sterilization time and energy costs. By contrast, steam sterilization may also require high amounts of energy (and incur greater costs) for commercial-scale bioreactor systems. Steam generation is also monitored in some localities by regulatory bodies that may require permits and regular inspections.

I. Systems

Described herein are systems that include one or more of the components suitable for growing a cell-based product such as a comestible meat product using the devices described herein. For example, the systems described herein may support, grow, separate, and recover cells cultured on a substrate of an enclosed vessel such as a bioreactor. Generally, the systems described herein include one or more of a bioreactor, fluid pump, fluid source, and controller (including memory, a processor, and associated computer instructions). For example, FIG. 1A is an illustrative block diagram of a system (100) comprising a bioreactor (110), an enclosed vessel (120), a fluid pump (130), a fluid conduit (132), a fluid source (140), a controller (150), and one or more sensors (160).

In some variations, the fluid pump (130) may be configured to circulate a sterilant through one or more of a bioreactor and another enclosed vessel (e.g., mixing vessel) coupled to the bioreactor. In some variations, the fluid pump may be further configured to provide fluid flow of growth media (e.g., cell culture media, nutrients, liquid, water) through a bioreactor system. In some variations, the controller may be configured to control one or more of the fluid pump, bioreactor, enclosed vessel, and sensors. For example, the controller may be configured to control the fluid flow rate generated by the fluid pump, mixing generated by a mixing vessel, and environmental conditions within the bioreactor (e.g., temperature, pressure).

Figure 1B:
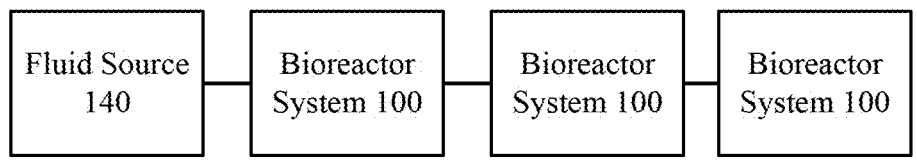

In some variations, a bioreactor system may comprise a plurality of bioreactors in fluid communication with each other and configured for efficient sterilization. FIG. 1B is an illustrative block diagram of a system (102) comprising a plurality of bioreactor systems (100) arranged in a tandem (e.g., serial) configuration. In some variations, a sterilant generated by a fluid source (140) may be circulated through a plurality of bioreactor systems (100) to sterilize the bioreactor systems more efficiently. For example, the same sterilant (e.g., sterilant gas) may be circulated through each system (100), thereby reducing energy usage.

Figure 1C:
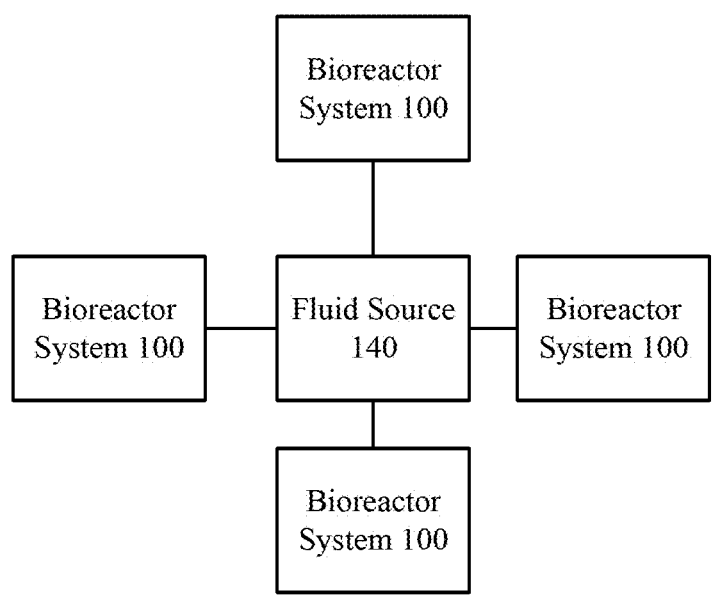

FIG. 1C is an illustrative block diagram of a system (104) comprising a plurality of bioreactor systems (100) arranged in a hub-spoke (e.g., parallel) configuration. In some variations, a sterilant generated by a fluid source (140) may be circulated simultaneously through each bioreactor system (100) for sterilization. For example, the bioreactor systems (100) may be sterilized simultaneously using the fluid source (140) to reduce sterilization times. In some variations, a system may comprise a combination of a tandem and hub-spoke configuration.

Figure 1D:
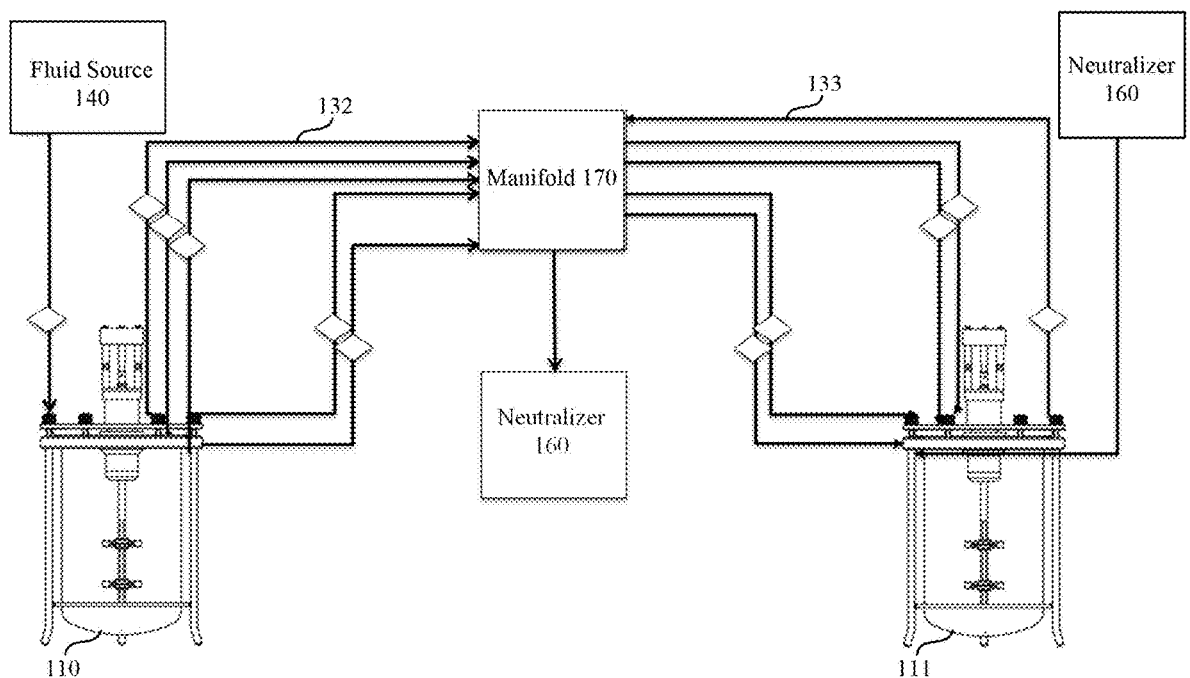

FIG. 1D is an illustrative block diagram of a system (106) comprising a plurality of bioreactors (110, 110). For example, a first bioreactor (110) may be coupled in series to a second bioreactor (111) via a manifold (170) and respective fluid conduits (132, 133). The fluid source (140) may be configured to generate a sterilant that may be circulated in series through the first bioreactor (110), manifold (170), second bioreactor (111), and neutralizer (160). In some variations, the neutralizer (160) may comprise an active carbon scrubber configured to neutralize the sterilant (e.g., sterilant gas, chlorine dioxide gas). In some variations, the manifold (170) and fluid conduits (132, 133) may be configured such that the sterilant may flow through each port of the bioreactors (110), (111) to ensure complete sterilization. In some variations, the second bioreactor (111) and corresponding fluid conduits (133) may comprise a mirror configuration relative to the first bioreactor (110) and fluid conduits (132).

Bioreactor

As described herein, a bioreactor may be configured to generate a variety of mechanical and fluid dynamic forces to enable long-term growth (e.g., days, weeks, months) of a cell culture (e.g., comestible meat product) in a sealed three-dimensional environment. For example, the bioreactor may be configured to grow one or more of a cell-based product and protein-based product. In some variations, the bioreactor may be configured to grow cells in one or more of a suspension and adherent (e.g., monolayer, multilayer) culture.

In some variations, the bioreactor (110) may comprise one or more of a port (112) (e.g., inlet port, outlet port), substrate (114), agitator (116), and cells (118) (e.g., cell culture). For example, a cell culture (118) may be disposed and grown on one or more of the substrates (114) of the bioreactor (110). In some variations, the bioreactor (110) may be coupled to one or more of a fluid pump (130), fluid conduit (132), fluid source (140), controller (150), and one or more sensors (160). In some variations, the bioreactor may be configured to be operated in one or more modes comprising a batch mode, a fed batch mode, a perfusion mode, a semi-continuous mode, and a continuous mode, or any suitable mode.

In some variations, one or more portions of the bioreactor (110) may be sterilizable such as a bioreactor enclosure, substrate (114), agitator (116), and the like. In some variations, one or more components of the bioreactor (110) or enclosed vessel that are sensitive to sterilization may be configured to be removable from the system (100). For example, a scaffold of a substrate (114) may be removed from the bioreactor (110) prior to sterilization. Additionally or alternatively, one or more components of the bioreactor (110) may be disposable after a predetermined number of uses. In some variations, any of the components of the bioreactor may be substantially non-degradable.

In some variations, a plurality of bioreactors (110) may be coupled in fluid communication with each other via corresponding fluid conduits (132). This may allow the plurality of bioreactors (110) to be sterilized together by, for example, circulating a sterilant through each of the bioreactors configured in a serial and/or parallel configuration, thereby streamlining the sterilization of the system (100).

The components of the bioreactor (e.g., enclosure, substrates, agitator) may be composed of a material including, but not limited to, one or more of polychlorotrifluoroethylene, polyetherimide, polysulfone, polystyrene, polycarbonate, polypropylene, silicone, polyetheretherketone, polymethylmethacrylate, nylon, acrylic, polyvinylchloride, vinyl, phenolic resin, petroleum-derived polymers, glass, polyethylene, terephthalate, metal, stainless steel, titanium, aluminum, cobalt-chromium, chrome, silicates, glass, alloys, ceramics, carbohydrate polymer, mineraloid matter, and combinations or composites thereof.

Enclosure

In some variations, a bioreactor (100) may comprise an enclosure configured to provide a sealed chamber to allow for the sterile growth of a comestible meat product. An enclosure may define a cavity therein. The enclosure may comprise one or more ports (e.g., inlets, outlets) configured to receive and/or output one or more of fluid (e.g., liquid, gas), cells, compositions, cell culture media, and the like. The enclosure may comprise at least a first port (110) (e.g., inlet) configured to receive fluid from, for example, a fluid conduit (132) coupled to a fluid source (140), and at least a second port (e.g., outlet) configured to output one or more of the fluid and a comestible meat product. For example, the outlet may comprise a sufficient size to output a meat product separated from one or more substrates (114) within the bioreactor (110). In some variations, an inlet may be disposed on a first side of the enclosure (e.g., top) and the outlet may be disposed on a second side of the enclosure (e.g., bottom) opposite the first side.

In some variations, a fluid pump (130) may be configured to be in fluid communication with one or more of the ports (112) via respective fluid conduits (132). In some variations, at least one port may be configured to both receive and output fluid including, but not limited to, liquid, gas, water, sterilant, combinations thereof, and the like. One or more ports may be configured for circulating sterilant gas. For example, the bioreactor may comprise a first port configured to splurge sterilant gas through fluid (e.g., liquid) disposed within a lower portion of the bioreactor (110) and a second port configured to circuit sterilant gas through a headspace (e.g., upper portion) of the bioreactor (110). In some variations, an inlet may be defined along an upper surface (e.g., top) or other upper region of the bioreactor (110) relative to a ground surface. This may allow fluid flow through the bioreactor (110) from a first elevation (e.g., height of the inlet) to a second elevation (e.g., height of an outlet) lower than the first elevation. This configuration may promote drainage and complete circulation of liquid fluid through the bioreactor (110). In some variations, the port (112) may be disposed on one or more sides (e.g., sidewalls) of the bioreactor (110). In some variations, the port (112) may comprise a connector (e.g., adapter, fitting) configured to couple to one or more of the fluid conduits (132).

In some variations, a port (112) may comprise a valve (not shown) configured to, for example, control fluid flow and prevent backflow of fluid into a fluid conduit (132). In some variations, a port (112) may be configured for different steps of a sterilization and/or meat production process. For example, different inlet(s) may be configured to enable passage of sterilant therethrough to sterilize surfaces of the bioreactor (110) and/or fluid (e.g., water) disposed within the bioreactor (110). The same or other inlet(s) may be configured to receive growth media (e.g., cell culture media) from an enclosed vessel such as a mixing vessel (e.g., vortex chamber) and/or to circulate a sterilant between coupled bioreactors.

In some variations, the bioreactor (110) may comprise dimensions comprising an internal cavity volume of at least 1 L. For example, the bioreactor may comprise an internal volume between about 25 L and about 200 L, between about 100 L and about 500 L, between about 500 L and about 1,000 L, between about 100 L and about 4,000 L, between about 100 L and about 5,000 L, between about 100 L and about 7,000 L, between about 100 L and about 10,000 L, between about 100 L and about 15,000 L, and between about 100 L and about 20,000 L, including all values and sub-ranges in-between.

In some variations, one or more portions of a bioreactor may be composed at least in part of a transparent or translucent material such as a polymer or glass that may enable visual confirmation of a sterilization, mixing, and/or growth process. For example, the bioreactor may be entirely composed of a transparent or translucent material, or include a window composed of a transparent or translucent material. As another example, the bioreactor may include a metal (e.g., stainless steel) body lined at least partially with a polymer or glass.

Substrate

One or more substrates (114) in the bioreactor (110) may allow for high-density growth of comestible meat and other cell-based products. In some variations, the bioreactor may be configured to grow cells that are on a microcarrier substrate and/or encapsulated in a substrate. In some variations, the amount of comestible meat prepared by a bioreactor system described herein may correspond to the number and surface area of the substrates (1140). For example, a plurality of substrates may be configured to generate a commercial-scale quantity of comestible meat. In some variations, a plurality of substrates may include up to about 1,000 substrates, including all values and sub-ranges in-between. In some variations, a spacing between adjacent (e.g., proximate) substrates may be between about 0.3 mm and about 5.0 cm, including all values and sub-ranges in-between. In some variations, each substrate may comprise an area between about 430 $cm^2$ and about 8,000 $cm^2$, up to about 500,000 $cm^2$, up to about 1,000,000 $cm^2$, up to about 2,000,000 $cm^2$, up to about 5,000,000 $cm^2$, and up to about 10,000,000 $cm^2$, including all values and sub-ranges in-between.

The substrates (114) described herein may be sized and shaped to be placed into and/or integral with the bioreactor (110). In some variations, a plurality of substrates (114) may be used in a predetermined arrangement. In some variations, a plurality of substrates (114) may be configured to releasably engage to the bioreactor (110) (e.g., through mating features, in guide slots, etc.). In some variations, one or more of the plurality of substrates (114) may be disposed in a vertical orientation or other non-zero orientation (e.g., at least 45 degrees, at least 60 degrees, at least 75 degrees, at least 85 degrees, etc.) relative to a ground surface such that fluid may be configured to flow downward in the spaces between the substrates.

In some variations, the substrates are planar. Additionally or alternatively, one or more substrates may be non-planar. For example, each substrate may comprise one or more of a rectangle, rod, bead, disk, spiral, coil, helix, corrugated, and sinusoidal shape (e.g., Raschig super rings). The substrates need not be parallel to one another, and may be angled and/or intersecting relative to one another. In some variations, a substrate may extend across one or more dimensions (e.g., length, width, diameter) of the enclosure to better utilize (e.g., maximize use of) an internal volume of the enclosure. In some variations, the substrates may be disposed in an ordered or non-ordered arrangement. In some variations, the substrates are configured to grow the meat product on opposite sides or faces of the substrate. In other variations, the substrates may be arranged in and/or are in conjunction with a three-dimensional lattice-like configuration that is exogenously provided (e.g., scaffold). For example, the substrates may include three-dimensional, porous and/or lattice-like structures. In other variations, the substrates do not comprise an exogenous scaffold, and are scaffold-less (e.g., exclude three-dimensional, porous and/or lattice-like structures that are not endogenously generated by the cells). The substrates described herein may be composed of one or more of a solid material and a semi-solid material (e.g., hydrogel).

In some variations, a comestible meat product grown on the substrates described herein may have a thickness (e.g., height) of at least about 1 µm. For example, the comestible meat product has a thickness in a range between about 1 µm and about 5 mm, between about 100 µm and about 1 mm, between about 200 µm and about 500 µm, and between about 300 µm and about 800 µm, including all values and sub-ranges in-between.

Agitator

In some variations, a bioreactor (110) and/or enclosed vessel (120) may comprise an agitator (e.g., impeller, rotator) (116) configured to stir (e.g., mix) one or more of gas, fluid, and compositions disposed therein. In some variations, a rate and/or duration of agitation may be based on one or more sensor measurements (e.g., mixing, turbidity, hydration, pH sensor, osmolality, conductivity). A controller (150) may be coupled to the agitator (116) and configured to control rotation of the agitator (116). In some variations, the controller may be configured to generate a first agitation signal to agitate fluid (e.g., water) in the bioreactor (110) when a sterilant gas is circulated in the fluid. In some variations, the controller may be configured to generate a second agitation signal to agitate a cell culture media introduced into the bioreactor (110). For example, a dehydrated cell culture media (e.g., dry powder media (DPM)) may be agitated until it becomes hydrated. In some variations, the agitator (116) may be configured to rotate at a rate between about 1 RPM and about 600 RPM.

Cells

The cells described herein may include, but are not limited to, cells comprising one or more of endoderm, mesoderm, ectoderm, and combinations thereof. In some variations, cells comprise one or more cells from livestock (e.g., bovine, porcine, ovine, caprine), poultry (e.g., avian), game, aquatic animal species, and the like. In some variations, cells comprise one or more of myoblasts, mesangioblasts, myofibroblasts, mesenchymal stem cells, hepatocytes, fibroblasts, pericytes, adipocytes, epithelial, chondrocytes, osteoblasts, osteoclasts, pericytes, pluripotent stem cells, somatic stem cells, and endothelial cells. The cell types described herein further encompass any of their states of differentiation. For example, the cells include a myoblast, myotube, mature skeletal muscle, fibroblasts, tissue that includes cells and secreted extracellular matrix, adipocytes, adipose tissue, epithelial cells, epithelial tissue, vascular endothelium, combinations thereof, and the like. In some variations, cells may comprise vertebrate cells or non-vertebrate cells. In some variations, cells may comprise one or more of mammalian, yeast, and bacterial cells. In some variations, cells may comprise non-mammalian cells (e.g., insect cells, avian cells, fish cells, reptile cells, invertebrate cells). In some variations, cells may be genetically altered from their native state (e.g., genetic insertion, deletion or recombination). Examples of genetic alterations include cells that are engineered to overexpress a myogenic transcription factor. The cells may exist in different ratios, for example. In some variations, the devices, systems, and methods disclosed herein may comprise the description in International Publication No. WO 2015/066377, filed on Oct. 30, 2014, International Publication No. WO 2017/124100, filed on Jan. 17, 2017, International Publication No. WO 2018/208628, filed on May 5, 2018, International Publication No. WO 2019/014652, filed on Jul. 13, 2018, International Application Serial No. PCT/US2020/034949, filed May 28, 2020, and U.S. Patent Application Ser. No. 62/938,087, filed Nov. 20, 2019, the contents of each of which are hereby incorporated by reference in its entirety.

Fluid Source

In some variations, a fluid source (e.g., reservoir) may be coupled to a fluid pump and enclosed vessel (e.g., bioreactor, mixing vessel) for sterilization and/or preparing a meat product. The fluid source is configured to store fluid. In some variations, distinct fluid sources may be configured to generate and/or store a respective sterilant gas, a non-sterilant gas, liquid (e.g., water), and growth media comprising one or more cells. For example, a first fluid source may be configured to generate and/or store a sterilant gas or vapor such as chlorine dioxide. A second fluid source may be configured to store different fluid compositions for different growth stages of a meat product. The second fluid source may be configured to store recirculated media and separately store fresh media. A third fluid source may be configured to store water used to hydrate the growth media. In some variations, one or more sensors may be coupled to the fluid source to measure one or more parameters of the fluid such as pH, dissolved gas concentration, osmolality, turbidity, hydration, conductivity, absorbance, nutrient concentration, waste concentration, ion concentration, oxygen concentration, and temperature. In some variations, chlorine dioxide gas concentration may be measured using a photometer configured to measure absorbance of the gas.

As shown in FIG. 1, one or more fluid pumps (130) may be in fluid communication with the bioreactor (110), enclosed vessel (120), and fluid source (140). The fluid source (140) (e.g., fluid reservoir) may be configured to store fluid (142) (e.g., sterilant, growth media, cells, liquid, and combinations thereof). For example, the system (100) may comprise a plurality of fluid sources (140) including a sterilant fluid source configured to generate chlorine dioxide gas (or other sterilant gas or vapor), a non-sterilant gas source configured to store a non-sterilant gas (e.g., air, $N_2$ gas, $O_2$ gas, $CO_2$ gas), and a fluid reservoir configured to store a fluid such as water (e.g., purified water). The fluid pump (130) may be configured to pump and/or recirculate the fluid (142) through a set of fluid conduits (132) forming a closed circuit (closed-loop path) of the system (100). For example, predetermined fluid conduits (132) may be coupled to respective fluid pumps (130) and fluid reservoirs (140) for circulating predetermined fluids (142) (e.g., sterilant gas, sterilant vapor, water, growth media compositions) to the bioreactor (110) to perform one or more sterilization and cell growth steps. In some variations, the bioreactor (110) may be coupled to a plurality of controllers (150). For example, a set of sensors (160) may be coupled to respective sensor controllers.

Fluids

As used herein, the fluid that may circulate throughout the system may comprise one or more of a sterilant gas or vapor, non-sterilant gas or vapor, liquid, water, growth media (e.g. cell culture media), nutrients, metabolites, signaling factors, and compositions configured for meat product growth. In some variations, the fluid may further comprise cells used to seed the substrates of the bioreactor that grow the comestible meat product.

In some variations, a fluid may comprise an additive comprising one or more of an amino acid, anti-foaming agent, shear protectant, protein, nutrient mixture, mammalian cells, bacteria, virus, yeast, and insect cells. In some variations, one or more of the additives may be introduced into a bioreactor after removing a sterilant (e.g., sterilant gas or vapor, chlorine dioxide).

Sterilant

In some variations, the sterilants described herein may be configured to be circulated within one or more of a bioreactor and enclosed vessel for a dwell time sufficient to sterilize one or more of the bioreactor, vessel, and contents disposed therein (e.g., cell culture media, fluid). In some variations, the sterilant may comprise a sterilant gas such as chlorine dioxide. In some variations, a sterilant may comprise one or more of chlorine dioxide ($ClO_2$) gas, ethylene oxide gas, hydrogen peroxide vapor, and peracetic acid vapor. FIG. 2 depicts a table of example sterilants that may be used and their properties.

Chlorine dioxide gas is a true gas at room temperature such that it may naturally diffuse within an enclosed volume to sterilize all exposed surfaces and compositions disposed within the system. That is, chlorine dioxide may fill an enclosed volume evenly and completely. Sterilants that are not true gases may not diffuse evenly and thus may have difficulty in sterilizing portions of a bioreactor comprising small volumes, tight corners, tortuous paths, and the like (however, certain sterilant vapors may be sufficient for sterilization). Chlorine dioxide gas is generally yellowish-green in color with a solubility of about 20 g/L in water. Chlorine dioxide gas sterilizes through oxidation rather than through chlorination. Chlorine dioxide is also effective in penetrating and sterilizing water. Chlorine dioxide is also not considered a carcinogen.

Chlorine dioxide gas further does not leave a residue on either organic or inorganic matter after sterilization, which may improve the results of the sterilization methods described herein. Dehydrated cell culture media (e.g., dry powder media) sterilized using a sterilant gas which is not a true gas may become moist. Clumps of dry powder media may form when the moist dry powdered media is hydrated (such as in a mixing vessel and/or bioreactor). The hydrated cell culture media may benefit from additional mixing to ensure that the media is fully solubilized. Therefore, chlorine dioxide gas may improve the efficiency of cell culture media sterilization.

In some variations, a fluid source (140) may be configured to generate chlorine dioxide gas. For example, chlorine dioxide may be generated by reacting sodium chlorite with chlorine gas or by mixing sodium chlorite with sodium hypochlorite and hydrochloric acid.

In some variations, a sterilant gas may be a more effective than a sterilant liquid in ensuring sterilization coverage since a sterilant liquid flowing through a bioreactor system may not contact all the surfaces within a bioreactor. For example, air bubbles may form within the sterilant liquid such that portions of the bioreactor in contact with the air bubbles may not be sterilized completely.

Culture Media

In some variations, cell culture media may comprise liquid cell culture media or dehydrated cell culture media. Dehydrated cell culture media or dry powder media (DPM) may comprise a mixture of amino acids, salts, glucose and other chemicals necessary for the growth of cells. In some variations, DPM is milled to particles of a predetermined size and mixed together. DPM may be hydrated with a liquid such as purified water to form liquid cell culture media. Conventionally, liquid cell culture media may be passed through a sterilization filter before being provided to cells in a bioreactor.

In some variations, the cell culture media may comprise a complete composition sufficient to grow cells by itself without any other additions. That is, complete cell culture media contains all components necessary for the growth of cells being grown in the bioreactor. In some variations, the cell culture media may comprise an incomplete composition configured to grow cells with the addition of at least one other composition. In some variations, a complete cell culture media may comprise one or more of water, buffer, and nutrients that support cell growth. For example, an incomplete cell culture media composition may be formed without components sensitive to oxidation. The incomplete cell culture media may be sterilized within the bioreactor and any oxidation sensitive components necessary to grow the cells may be added to the bioreactor system after sterilization. For example, an amino acid may not be included in the incomplete cell culture media that is sterilized, and may be added to a bioreactor thereafter. In some variations, the pH of the incomplete cell culture media may be different than the pH of the complete cell culture media.

Fluid Pump

In some variations, one or more fluid pumps (130) may be coupled to a fluid conduit (1332) in fluid communication with a bioreactor (110) to generate a predetermined fluid flow rate through the bioreactor (110) to circulate a sterilant and/or aid growth of a comestible meat product. In some variations, a fluid pump may comprise one or more of a positive displacement pump (e.g., peristaltic pump), centrifugal pump, combinations thereof, and the like. One or more fluid sources may be coupled to the fluid pump.

In some variations, the fluid pump may be configured to receive a fluid pump signal (generated by a controller) configured to circulate a sterilant in the bioreactor and/or mixing vessel for a dwell time sufficient to sterilize cell culture media such as dehydrated cell culture media (dry media powder). For example, the fluid pump may be configured to circulate the sterilant for at least one minute.

In some variations, the fluid pump may be configured to receive a fluid pump signal configured to circulate the fluid from the bioreactor to the mixing vessel to hydrate the sterilized cell culture media. In some of these variations, the second fluid pump signal may be configured to circulate the fluid to generate a fluid vortex in a mixing vessel.

In some variations, the fluid pump may be configured to receive a fluid pump signal configured to circulate a non-sterilant gas into the bioreactor and/or mixing vessel to remove the sterilant from the bioreactor and/or mixing vessel.

In some variations, the fluid pump may be configured to operate over extended periods of time (e.g., days, weeks). For example, the fluid pump may be configured to pump fluid for at least 1 day (e.g., 3, 5, 10, 15, 20, 25, 30 days).

Enclosed Vessel

An enclosed vessel (120) of a bioreactor system (100) may comprise any sealed chamber in fluid communication with a bioreactor (110). For example, the enclosed vessel (120) may comprise one or more of a second bioreactor and a mixing vessel. In some variations, a mixing vessel may be configured to mix two or more substances (e.g., fluids, compositions).

In some of these variations, a mixing chamber may comprise a vortex chamber. Generally, a vortex chamber may be configured to quickly mix substances at a high velocity. For example, fluid may be into a vortex chamber tangentially along an inner circumference of the chamber. Under the principles of conservation of angular momentum, an input fluid may be configured to accelerate towards an outlet port. In this manner, fluid may be homogenized quickly (e.g., on the order of milliseconds). In some variations, the mixing chamber may comprise a cylindrical or conical shape.

Figure 3:
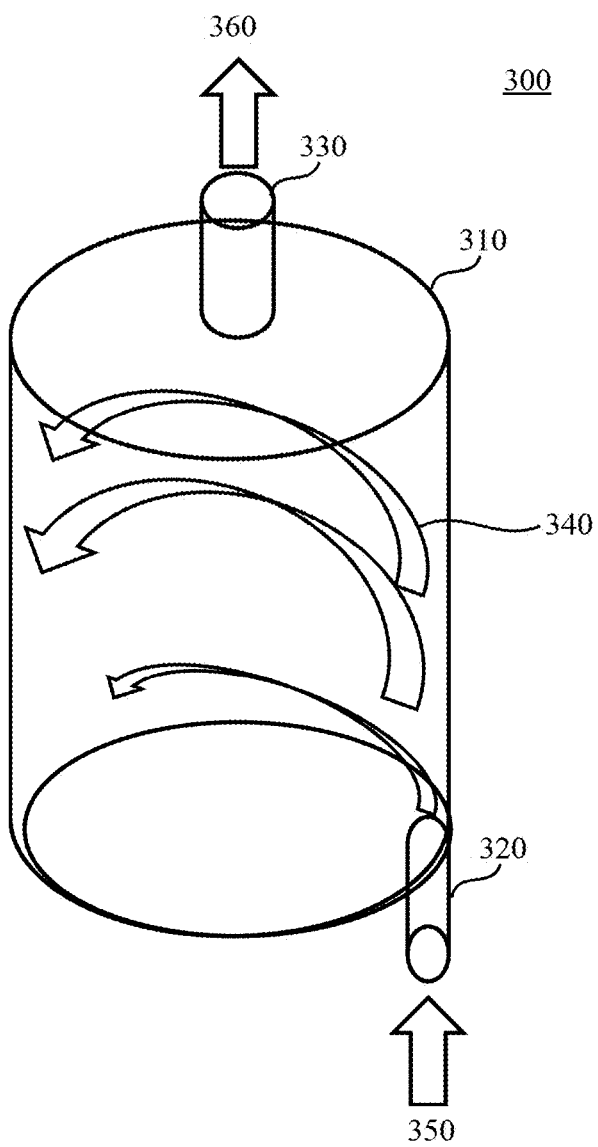
FIG. 3 is a perspective view of an illustrative variation of a mixing vessel.

FIG. 3 is a perspective view of a mixing vessel (300) comprising an enclosure (310), inlet (320), and outlet (330). Fluid (350) may flow through the mixing vessel (300) along a centrifugal path (340). In some variations, a fluid (e.g., liquid) (350) enters the mixing vessel (300) through an inlet (320) disposed at an angle tangent to an interior surface of the enclosure (310). A velocity of the liquid (350) entering the mixing vessel (300) may correspond to a fluid stream pressure which may depend on a diameter of the inlet (320) and the dimensions of the vessel (350). For example, a smaller inlet (320) diameter may correspond to higher liquid velocity and vice versa. The mixing vessel (300) may be configured such that the velocity of the liquid (350) may be sufficient to for the liquid (350) follows the inner surface of the enclosure (310) along the path (340). A turbulent vortex may be generated when the rotational fluid velocity of the liquid (350) reaches a predetermined threshold. The turbulent vortex may be configured to mix the liquid (350) with a composition (e.g., dry powder media) (not shown) disposed in the enclosure (310). The mixed contents (360) of the vessel (300) may exit the enclosure (310) from the outlet (330). The outlet (330) may be disposed at a top of the mixing chamber (300). The outlet (330) may be coupled to an inlet of a bioreactor. In some variations, the dry powder media may be disposed in the mixing vessel (300) prior to sterilization.

Figure 4A:
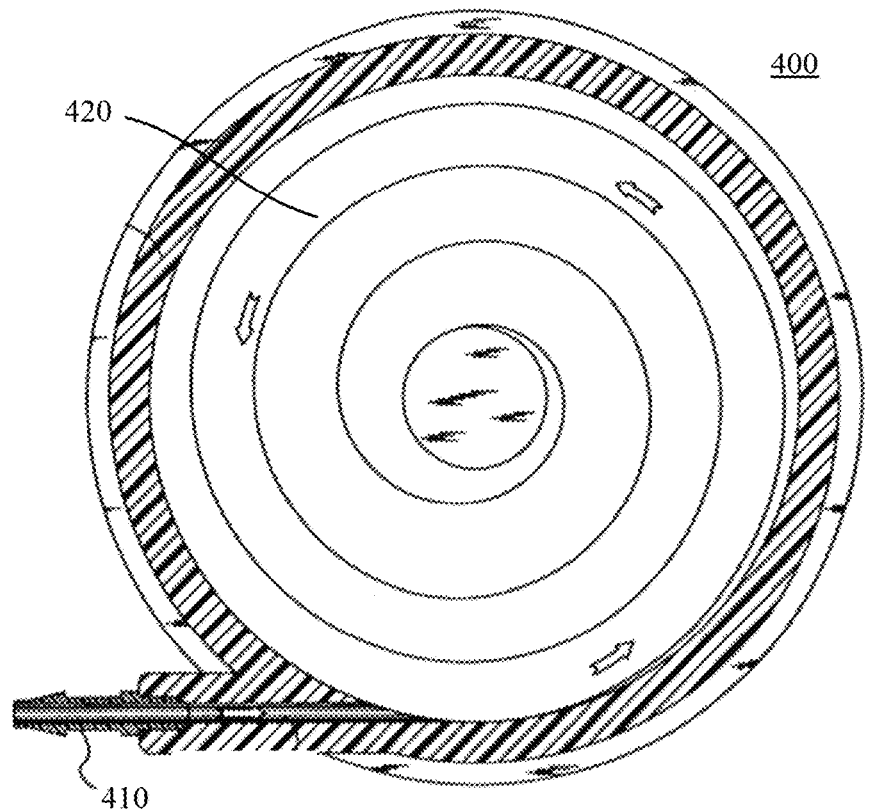
FIGS. 4A and 4B are plan views of illustrative variations of a mixing vessel.
Figure 4B:
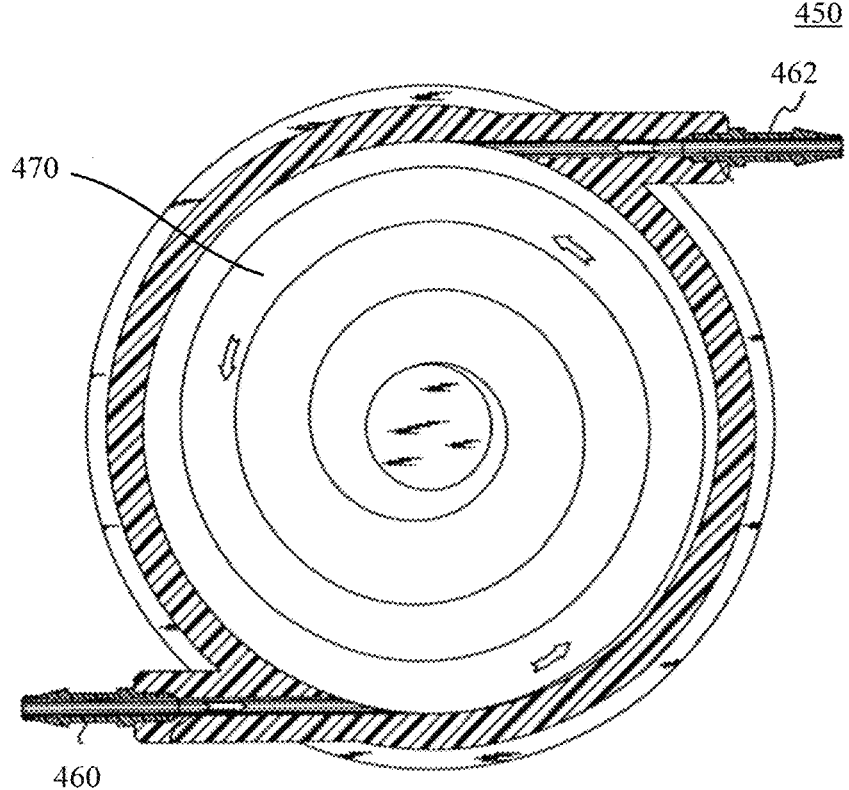

FIGS. 4A and 4B are plan cross-sectional views of mixing vessel (400, 450) variations. FIG. 4A depicts a mixing vessel (400) comprising an inlet (410) and a fluid path (420). FIG. 4B depicts a mixing vessel (450) comprising a first inlet (460), a second inlet (462), and a fluid path (470). In some variations, two or more inlets as shown in FIG. 4B may improve mixing (e.g., hydration) efficiency of dry powder media or a viscous solution. A fluid such as water may be introduced through the inlet (410, 460, 462). In some variations, different fluids may be introduced through each inlet. For example, purified water may be introduced through the first inlet (460) and sodium bicarbonate may be introduced through the second inlet (462). Each inlet may comprise a diameter based on the fluid introduced therein. In some variations, inlets may be disposed along a height of the mixing vessel in order to generate additional fluid velocity to promote vortex generation and improve mixing.

In some variations, one or more portions of a mixing vessel may be composed at least in part of a transparent or translucent material such as a polymer or glass that may enable visual confirmation of a sterilization and/or mixing process. For example, the mixing vessel may be entirely composed of a transparent or translucent material, or include a window composed of a transparent or translucent material.

Controller

Generally, the systems described herein may include at least one bioreactor for preparing a comestible meat product and corresponding controller coupled to at least one fluid pump and sensors. In some variations, a sensor may be configured to generate signal data. The signal data may be received by a controller and used to generate fluid pump signals to control the fluid pump. Additionally or alternatively, the controller (and/or other suitable controller(s)) may be configured to operate one or more valves and/or other suitable portions of the system.

Referring to FIG. 1, in some variations, a controller (150) may be coupled to one or more of a bioreactor (110), at least one enclosed vessel (120), at least one fluid pump (130), at least one fluid source (140), and one or more sensors (160). The controller (150) may comprise one or more of a processor (152), memory (154), input/output device (156), and communication device (158). In some variations, the controller (150) is configured to receive data from one or more of the bioreactor (110), fluid pump (130), fluid source (140), and sensors (160). In some variations, the sensors (160) may comprise one or more of a flow sensor, temperature sensor, pH sensor, dissolved gas sensor, pressure sensor, optical sensor, turbidity sensor, and the like. In some variations, the data may be processed and used to monitor and/or control one or more components of the system (100).

The controller may accordingly monitor and/or control sterilization and/or cell growth. As described in more detail herein, the controller (150) may be coupled to one or more networks using a communication device (158). The controller (150) may include a processor (152) and memory (154) coupled to an input device (156).

The controller (150) may include computer instructions for operation thereon to cause the processor (152) to perform one or more of the steps described herein. In some variations, the computer instructions may be configured to cause the processor to receive signal data from the sensors, generate fluid pump signals, and output data a user. The controller (150) may include one or more processors (152) and one or more machine-readable memory devices (154) in communication with the one or more processors (152). The processor (152) may incorporate data received from memory (154) and user input to control the system (100). The memory (154) may further store instructions to cause the processor (152) to execute modules, processes, and/or functions associated with the system (100). The controller (150) may be connected to and control one or more of sensor (160), fluid pump (130), communication device (158), and the like by wired and/or wireless communication channels.

The controller (150) may be implemented consistent with numerous general purpose or special purpose computing systems or configurations. Various exemplary computing systems, environments, and/or configurations that may be suitable for use with the systems and devices disclosed herein may include, but are not limited to software or other components within or embodied on a server or server computing devices such as routing/connectivity components, multiprocessor systems, microprocessor-based systems, distributed computing networks, personal computing devices, network appliances, portable (e.g., hand-held) or laptop devices. Examples of portable computing devices include smartphones, personal digital assistants (PDAs), cell phones, tablet PCs, wearable computers taking the form of smartwatches and the like, and portable or wearable augmented reality devices that interface with the patient's environment through sensors and may use head-mounted displays for visualization, eye gaze tracking, and user input.

The processor (152) may be any suitable processing device configured to run and/or execute a set of instructions or code and may include one or more data processors, image processors, graphics processing units, physics processing units, digital signal processors, and/or central processing units. The processor (152) may be, for example, a general purpose processor, Field Programmable Gate Array (FPGA), an Application Specific Integrated Circuit (ASIC), combinations thereof, and the like. The processor (152) may be configured to run and/or execute application processes and/or other modules, processes and/or functions associated with the system and/or a network associated therewith. The underlying device technologies may be provided in a variety of component types including metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, combinations thereof, and the like.

In some variations, the memory (154) may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, combinations thereof, and the like. As used herein, database refers to a data storage resource. The memory (154) may store instructions to cause the processor (152) to execute modules, processes, and/or functions associated with the controller (150), such as calibration, signal processing, sensor analysis, notification, communication, authentication, user settings, combinations thereof, and the like. In some variations, storage may be network-based and accessible for one or more authorized users. Network-based storage may be referred to as remote data storage or cloud data storage. Signal data and analysis stored in cloud data storage (e.g., database) may be accessible to authorized users via a network, such as the Internet. In some variations, database may be a cloud-based FPGA.

Some variations described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for a specific purpose or purposes.

Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs); holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other variations described herein relate to a computer program product, which may include, for example, the instructions and/or computer code disclosed herein.

The systems, devices, and methods described herein may be performed by software (executed on hardware), hardware, or a combination thereof. Hardware modules may include, for example, a general-purpose processor (or microprocessor or microcontroller), a field programmable gate array (FPGA), an application specific integrated circuit (ASIC), combinations thereof, and the like. Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

The input/output device (156) may permit a user to interact with and/or control the system (800) directly and/or remotely. For example, the input/output device (156) may be configured for a user to input commands and an output device for a user and/or other users (e.g., technicians) to receive output (e.g., view sample data on a display device) related to operation of the system (100). In some variations, a communication device (158) may permit the controller (150) to communicate with one or more of a network (e.g., Internet), remote server, and database as described in more detail herein.

The input/output device (156) may serve as a communication interface between a user (e.g., operator) and the controller (150). In some variations, the input/output device (156) may include an output device (e.g., touch screen and display) and be configured to receive input data and output data from one or more sensors, input device, output device, network, database, and server. For example, signal data generated by a sensor may be processed by processor (152) and memory (154), and output visually by one or more output devices (e.g., display). Signal data, sensor data, and/or meat product data may be received by controller (150) and output visually, audibly, and/or through haptic feedback through one or more output devices. As another example, user control of an input device (e.g., joystick, keyboard, touch screen) may be received by input/output device (156) and then processed by processor (152) and memory (154) to output a control signal to one or more components of the system (100). In some variations, the input/output device (156) may function as both an input and output device (e.g., a handheld controller configured to generate a control signal while also providing haptic feedback to a user).

An output device may output data and may include one or more of a display device, audio device, and haptic device. The display device may be configured to display a graphical user interface (GUI). The input/output device (156) may include an integrated display and/or video output that may be connected to output to one or more generic displays, including remote displays accessible via the internet or network. The output data may also be encrypted to ensure privacy and all or portions of the output data may be saved to a server or database. A display device may permit a user to view signal data, calibration data, tissue data, image data, cell sample data, system data, fluid data, patient data, and/or other data processed by the controller (150). In some variations, an output device may include a display device including at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, holographic display, combinations thereof, and the like.

An audio device may audibly output sensor data, meat product data, system data, alarms and/or warnings. For example, the audio device may output an audible warning upon malfunction of a fluid pump. In some variations, an audio device may include at least one of a speaker, piezoelectric audio device, magnetostrictive speaker, and/or digital speaker. In some variations, a user may communicate with other users using the audio device and a communication channel.

A haptic device may be incorporated into one or more of the input and output devices to provide additional sensory output (e.g., force feedback) to the user. For example, a haptic device may generate a tactile response (e.g., vibration) to confirm user input to an input device (e.g., joystick, keyboard, touch surface). In some variations, the haptic device may include a vibrational motor configured to provide haptic tactile feedback to a user. Additionally or alternatively, haptic feedback may notify a user of an error such as pump malfunction and/or fluid disconnection. This may prevent potential harm to the system.

Some variations of an input device may include at least one switch configured to generate a control signal. For example, the input device may be configured to control one or more pumps to control fluid flow rate. In some variations, the input device may include a wired and/or wireless transmitter configured to transmit a control signal to a wired and/or wireless receiver of a controller (150). For example, an input device may include a touch surface for a user to provide input (e.g., finger contact to the touch surface) corresponding to a control signal. An input device including a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In variations of an input device including at least one switch, a switch may include, for example, at least one of a button (e.g., hard key, soft key), touch surface, keyboard, analog stick (e.g., joystick), directional pad, pointing device (e.g., mouse), trackball, jog dial, step switch, rocker switch, pointer device (e.g., stylus), motion sensor, image sensor, and microphone. A motion sensor may receive user movement data from an optical sensor and classify a user gesture as a control signal. A microphone may receive audio and recognize a user voice as a control signal.

In some variations, the controller (150) may be in communication with other devices via one or more wired and/or wireless networks. The communication device (156) may facilitate communication with other devices over one or more external ports (e.g., Universal Serial Bus (USB), multi-pin connector) configured to couple directly to other devices or indirectly over a network (e.g., the Internet, wireless LAN).

In some variations, the communication device (156) may include a radiofrequency receiver, transmitter, and/or optical (e.g., infrared) receiver and transmitter configured to communicate with one or more devices and/or networks. The communication device (156) may communicate by wires and/or wirelessly. In some variations, the communication device (156) may include radiofrequency (RF) circuitry (e.g., RF transceiver) including one or more of a receiver, transmitter, and/or optical (e.g., infrared) receiver and transmitter configured to communicate with one or more devices and/or networks. RF circuitry may receive and transmit RF signals (e.g., electromagnetic signals). The RF circuitry converts electrical signals to/from electromagnetic signals and communicates with communications networks and other communications devices via the electromagnetic signals. The RF circuitry may include one or more of an antenna system, an RF transceiver, one or more amplifiers, a tuner, one or more oscillators, a digital signal processor, a CODEC chipset, a subscriber identity module (SIM) card, memory, and the like. A wireless network may refer to any type of digital network that is not connected by cables of any kind. Examples of wireless communication in a wireless network include, but are not limited to cellular, radio, satellite, and microwave communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, near-field communication (NFC), radio-frequency identification (RFID), Wireless Fidelity (Wi-Fi) (e.g., IEEE 802.11a, IEEE 802.11b, IEEE 802.11g, IEEE 802.11n), Voice over Internet Protocol (VoIP), Wi-MAX, a protocol for email (e.g., Internet Message Access Protocol (IMAP), Post Office Protocol (POP)), instant messaging (e.g., eXtensible Messaging and Presence Protocol (XMPP), Session Initiation Protocol for Instant Messaging, Presence Leveraging Extensions (SIMPLE), Instant Messaging and Presence Service (IMPS)), Short Message Service (SMS), or any other suitable communication protocol. Some wireless network deployments combine networks from multiple cellular networks or use a mix of cellular, Wi-Fi, and satellite communication.

In some variations, a wireless network may connect to a wired network in order to interface with the Internet, other carrier voice and data networks, business networks, and personal networks. A wired network is typically carried over copper twisted pair, coaxial cable, and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, wireless personal area networks (PAN) (e.g., Bluetooth, Bluetooth Low Energy), and virtual private networks (VPN). As used herein, network refers to any combination of wireless, wired, public, and private data networks that are typically interconnected through the Internet, to provide a unified networking and information access system.

II. Methods

Also provided herein are methods for sterilizing a bioreactor and culture medium. The methods described here may ensure sterile for production of a meat product using one or more bioreactors. Generally, the methods described herein include sterilizing a bioreactor system together with a cell culture media by circulating a sterilant (e.g., sterilant gas). In some variations, a method of preparing sterile cell culture media may include circulating a sterilant (e.g., sterilant gas) through dehydrated cell culture media.

Figure 5:
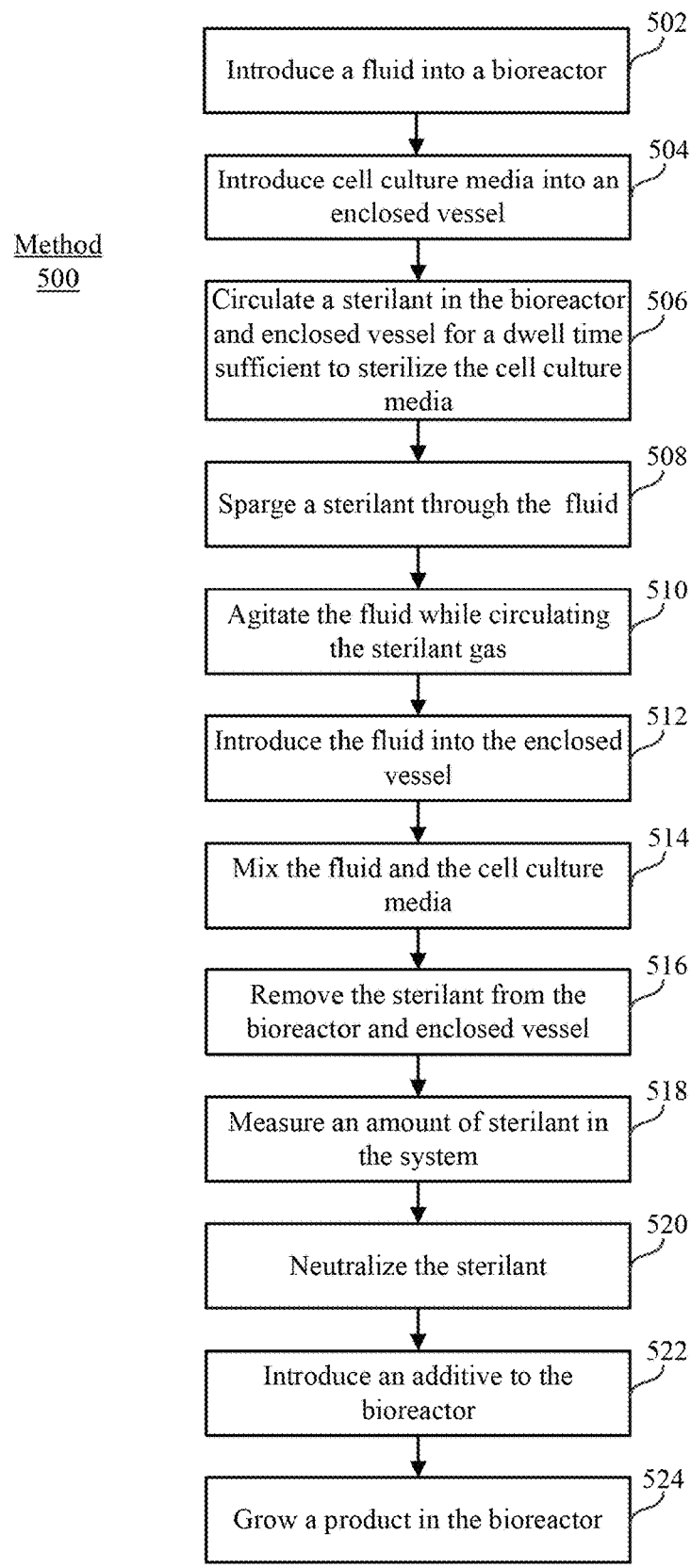
FIG. 5 is a flowchart of an illustrative variation of a method of sterilizing a bioreactor system.

FIG. 5 is a flowchart that generally describes a method (500) using any of the systems and devices described herein. The method (500) may include introducing a fluid into a bioreactor (502). For example, water may be introduced into a cavity of the bioreactor. In some variations, the bioreactor may be configured to grow a comestible meat product. Additionally or alternatively, the bioreactor may be configured to grow one or more of a cell-based product, protein-based product, mammalian, insect, yeast, and bacterial cells. In some variations, fluid may be introduced into a plurality of bioreactors (e.g., first bioreactor, second bioreactor, etc.). For example, as shown in FIG. 1B, a plurality of bioreactor systems receiving the fluid may be arranged in a tandem configuration (e.g., in series). As another example, as shown in FIG. 1C, a plurality of bioreactor systems receiving the fluid may be arranged in a hub-spoke configuration (e.g., in parallel).

In some variations, cell culture media may be introduced into an enclosed vessel (504). In some variations, the enclosed vessel may be in fluidic communication with the bioreactor. In some variations, the enclosed vessel may be a mixing vessel. In some variations, the cell culture media may comprise liquid cell culture media or dehydrated cell culture media.

In some variations, a sterilant may be circulated in the bioreactor and enclosed vessel for a dwell time sufficient to sterilize the cell culture media (506). In some variations, the sterilant may be circulated for a dwell time sufficient to sterilize the fluid in the bioreactor. In some variations, the dwell time may be at least about one minute (e.g., at least one minute, at least three minutes at least five minutes) or other suitable duration. In some variations, a sterilant may be circulated from a first bioreactor to a second bioreactor in fluidic communication with the first bioreactor. In some variations, the sterilant may comprise one or more of chlorine dioxide gas, ethylene oxide gas, hydrogen peroxide vapor, and peracetic acid vapor.

In some variations, a sterilant may be sparged through the fluid in the bioreactor to sterilize the fluid (508). In some variations, the fluid in the bioreactor may be agitated while circulating the sterilant to further sterilize the fluid (510).

In some variations, fluid may introduced into the enclosed vessel to hydrate a cell culture media (512). In some variations, fluid and cell culture media may be mixed in the enclosed vessel (514). For example, the enclosed vessel may be a mixing vessel.

After the predetermined dwell time, the sterilant may be removed from the bioreactor and enclosed vessel (516). For example, one or more non-sterilant gases or other non-sterilant substances may be circulated in the bioreactor and the enclosed vessel to push or otherwise displace the sterilant out of the system. In some variations, an amount (e.g., volume) of sterilant remaining in the bioreactor system may be measured (518), such as by measuring the amount of sterilant being removed (e.g., as it exits the bioreactor system) (518) and determining the amount of sterilant remaining as the difference between the amount of sterilant originally introduced into the bioreactor system and the amount of sterilant removed from the bioreactor system. Sterilization may be considered completed when a sterilant level in the bioreactor system is at or below a predetermined threshold (e.g., 0 PPM). In some variations, a sterilization completion notification may be generated when sterilization is completed. In some variations, the sterilant may additionally or alternatively be neutralized (520). For example, the sterilant may be neutralized by an active carbon scrubber.

In some variations, an additive may be introduced to the bioreactor (522). For example, one or more additives may be introduced to the bioreactor after removing the sterilant gas. The additive may comprise one or more of an amino acid, anti-foaming agent, shear protectant, protein, nutrient mixture, mammalian cells, bacteria, yeast, and insect cells.

In some variations, a product may be grown in the bioreactor (524). In some variations, the bioreactor may be operated in one or more modes comprising batch, fed batch, perfusion, semi-continuous, and continuous. In some variations, the bioreactor may be configured to grow cells in one or more of a suspension and monolayer culture. In some variations, the bioreactor may be configured to grow cells on one or more of a microcarrier substrate and encapsulated in a substrate.

Figure 6:
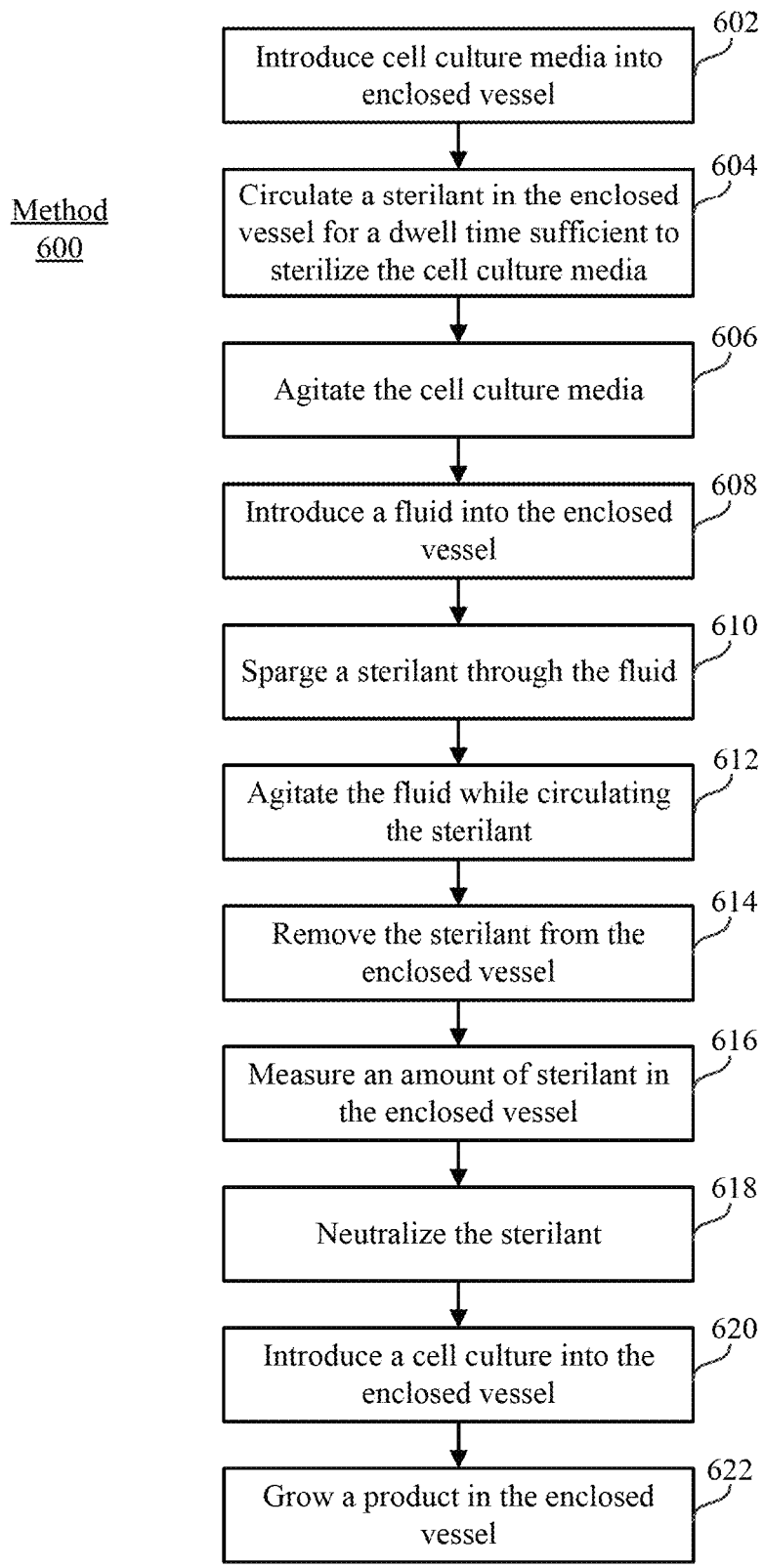
FIG. 6 is a flowchart of an illustrative variation of a method of preparing cell culture media.

FIG. 6 is a flowchart that generally describes a method (600) of preparing cell culture media using any of the systems and devices described herein. The method (600) may include introducing a fluid into an enclosed vessel (602). In some variations, the cell culture media may comprise a complete composition configured to grow cells by itself. In some variations, the cell culture media may comprise an incomplete composition configured to grow cells with an addition of at least one other composition.

In some variations, the enclosed vessel may comprise one or more of a bioreactor and mixing vessel. In some variations, the bioreactor may be configured to grow a comestible meat product. Additionally or alternatively, the bioreactor may be configured to grow one or more of a cell-based product, protein-based product, mammalian, insect, yeast, and bacterial cells.

In some variations, a sterilant may be circulated in the enclosed vessel for a dwell time sufficient to sterilize the cell culture media (604). For example, a chlorine dioxide gas may be circulated in an enclosed vessel comprising dehydrated cell culture media. The chlorine dioxide gas may be circulated for a dwell time sufficient to sterilize the dehydrated cell culture media. In some variations, the dwell time may be at least about one minute. In some variations, the chlorine dioxide gas may be introduced and circulated into a headspace of the enclosed vessel.

In some variations, the cell culture media may be agitated (606). In some variations, a fluid may be introduced into the enclosed vessel (608). For example, a fluid may be introduced into the enclosed vessel to hydrate the sterilized cell culture media. In some variations, the enclosed vessel is a mixing vessel configured to mix the cell culture media. For example, a vortex flow may be generated in the enclosed vessel. The fluid may comprise water. In some variations, a sterilant may be sparged through the fluid (610).

In some variations, a fluid may be agitated while circulating the sterilant (612). In some variations, the sterilant may be removed from the enclosed vessel (614). For example, one or more non-sterilant gases may be circulated in the bioreactor and the enclosed vessel to push the sterilant out of the system. In some variations, one or more non-sterilant gases may be circulated in a headspace of the enclosed vessel. In some variations, an amount of sterilant may be measured in the enclosed vessel (616). Sterilization may be completed when a sterilant level reaches a predetermined threshold. In some variations, the sterilant may be neutralized (618).

In some variations, a cell culture may be introduced into the enclosed vessel (620) such as a bioreactor. In some variations, the sterilized cell culture media may be introduced into the bioreactor. In some variations, a product may be grown in the enclosed vessel (622). In some variations, the enclosed vessel is a bioreactor configured to grow a comestible meat product. In some variations, the bioreactor may be operated in one or more modes comprising batch, fed batch, perfusion, semi-continuous, and continuous. In some variations, the bioreactor may be configured to grow cells in one or more of a suspension and adherent culture. In some variations, the bioreactor may be configured to grow cells on one or more of a microcarrier substrate and encapsulated in a substrate.

Figure 7A:
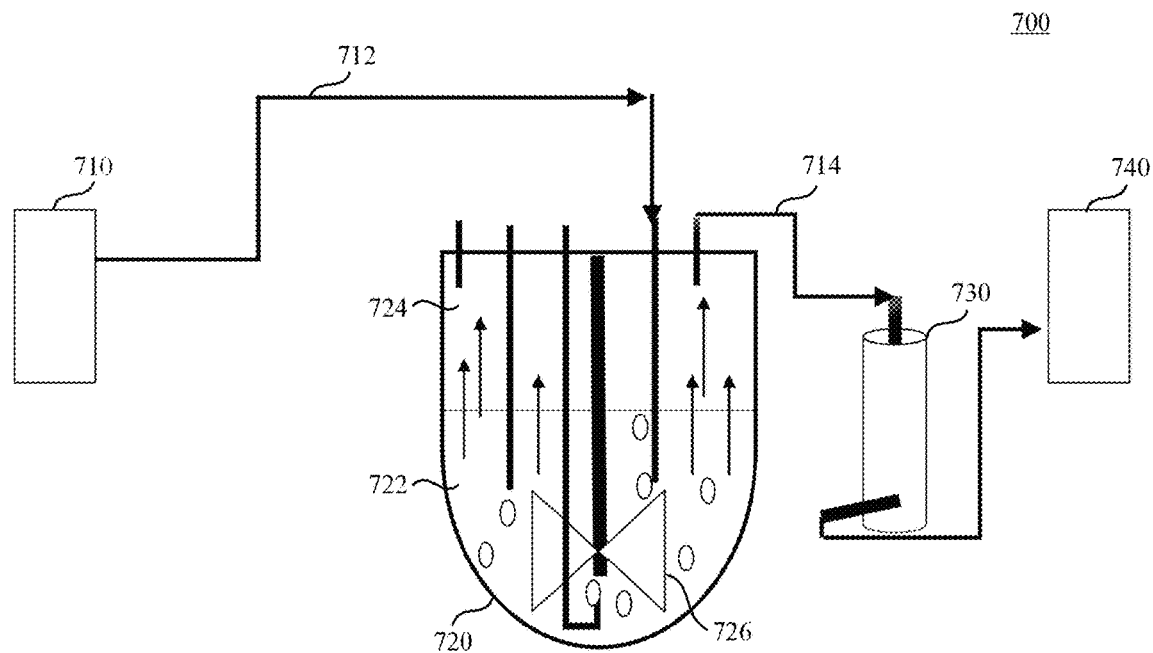
FIGS. 7A and 7B are schematic diagrams of an illustrative variation of a bioreactor system.
Figure 7B:
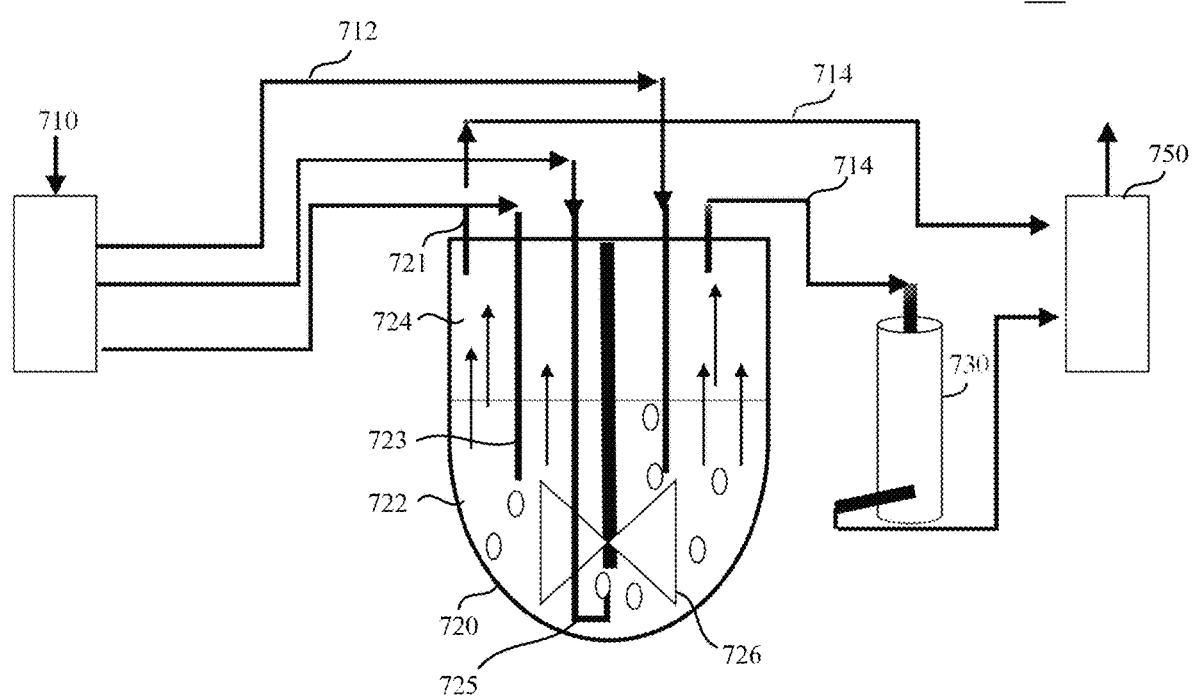

FIGS. 7A and 7B are schematic diagrams of a bioreactor system (700, 702) comprising a fluid source (710) (e.g., sterilant source), bioreactor (720), enclosed vessel (730) (e.g., mixing vessel, vortex chamber), and fluid reservoir (740) (e.g., gas outlet). In some variations, the fluid source (710) may comprise as a chlorine dioxide gas generator. The bioreactor (720) may be configured to grow a comestible meat product. The enclosed vessel (730) may be configured to hydrate dehydrated cell culture media, and the fluid reservoir (740) may be configured to remove and/or neutralize sterilant that has passed through the bioreactor system (700). In some variations, the fluid source (710), bioreactor (720), enclosed vessel (730), and fluid reservoir (740) may be in fluid communication via a set of fluid conduits (712, 714). For example, a sterilant such as chlorine dioxide gas generated by the fluid source (710) may be circulated in the bioreactor (720) and enclosed vessel (730). In some variations, the sterilant may be sparged into a fluid (722) disposed within the bioreactor (720) and circulated within a headspace (724) of the bioreactor (720) in order to sterilize the bioreactor (720) and fluid (722). In some variations, an agitator (726) may be configured to rotate and stir the fluid (722) as the sterilant is being sparged. After sterilization has been completed, the sterilant may be removed from the bioreactor (720) and enclosed vessel (730) via the fluid conduit(s) (714).

In some variations, a method of sterilization may include the steps of introducing a fluid (722) into the bioreactor (720). Cell culture media (e.g., dry powder media, dehydrated cell culture media) may be introduced into the enclosed vessel (730). A sterilant (e.g., sterilant gas) may be circulated into the bioreactor (720) and enclosed vessel (730) until a desired concentration and dwell time is reached. Then, a non-sterilant gas may be circulated into the bioreactor (720) and enclosed vessel (730) to displace the sterilant gas. For example, sterile air may flush out the sterilant gas. A dissolved oxygen sensor may be used to determine when the sterilant has been removed from the bioreactor (720) and the enclosed vessel (730). In some variations, the bioreactor (720) and enclosed vessel (730) may be in fluidic communication with a plurality of bioreactors (750) such that sterilant may be circulated for simultaneous sterilization. In other words, a plurality of bioreactors (720) may be placed in series (e.g., "daisy-chained") to increase sterilization efficiency (see FIG. 1D). Fluid conduits (712) may couple the bioreactors and enclosed vessels through any suitable configuration that allows sterilant gas circulation.

In some variations, the bioreactor (720) may comprise one or more ports (e.g., sample port, sterilant port, cell port). FIG. 7B depicts a bioreactor system (702) similar to system (700) except for additional fluid conduits (712, 714) to allow simultaneous circulation of sterilant (e.g., sterilant gas) through the fluid (722) and headspace (724).

In some variations, a method of sterilization may include the steps of rotating an agitator and pumping sterilant at a high enough rate to generate a vortex flow in the enclosed vessel (730) to hydrate dehydrated cell culture media disposed within the enclosed vessel (730). The hydrated cell culture media may then be introduced into the bioreactor (720). One or more additives may be introduced into the bioreactor (720). Sensor measurements may be taken of one or more of the bioreactor (720), fluid (722), and cell culture media. Growth conditions within the bioreactor (720) may be set. For example, temperature and pH may be adjusted to predetermined values. One or more cells may be introduced into and grown in the bioreactor (720).

In some variations, a method of sterilization may include washing, rinsing, and drying bioreactor (720) and/or enclosed vessel (730). In some variations, an upper portion (e.g., headplate) of the bioreactor (720) may comprise a gas outlet port (721) and a sample port (723). The bioreactor may comprise one or more additional ports configured for growing cells. In some variations, water (e.g., deionized water) may be introduced into the bioreactor (720) and cell culture media (e.g., dry culture media, dehydrated cell culture media) may be introduced into the enclosed vessel (730). In some variations, a fluid conduit (714) (e.g., thermoplastic elastomer (TPE)) may be coupled (e.g., welded) between the bioreactor (720) and the enclosed vessel (730). In some variations, a sterilant may be circulated through the bioreactor (720) through one or more of the ports until the sterilant reaches a predetermined concentration for a predetermined dwell time. For example, sterilant may be sparged through one or more of a gas inlet port (725) and sample port (723) such that sterilant will sterilize the bioreactor (720) and any contents (e.g., fluid (722)) disposed therein. In some variations, the sterilant may be displaced from the bioreactor (720) and enclosed vessel (730) by circulating a non-sterilant (e.g., sterile air) through the bioreactor (720) and the enclosed vessel (730).

Figure 8:
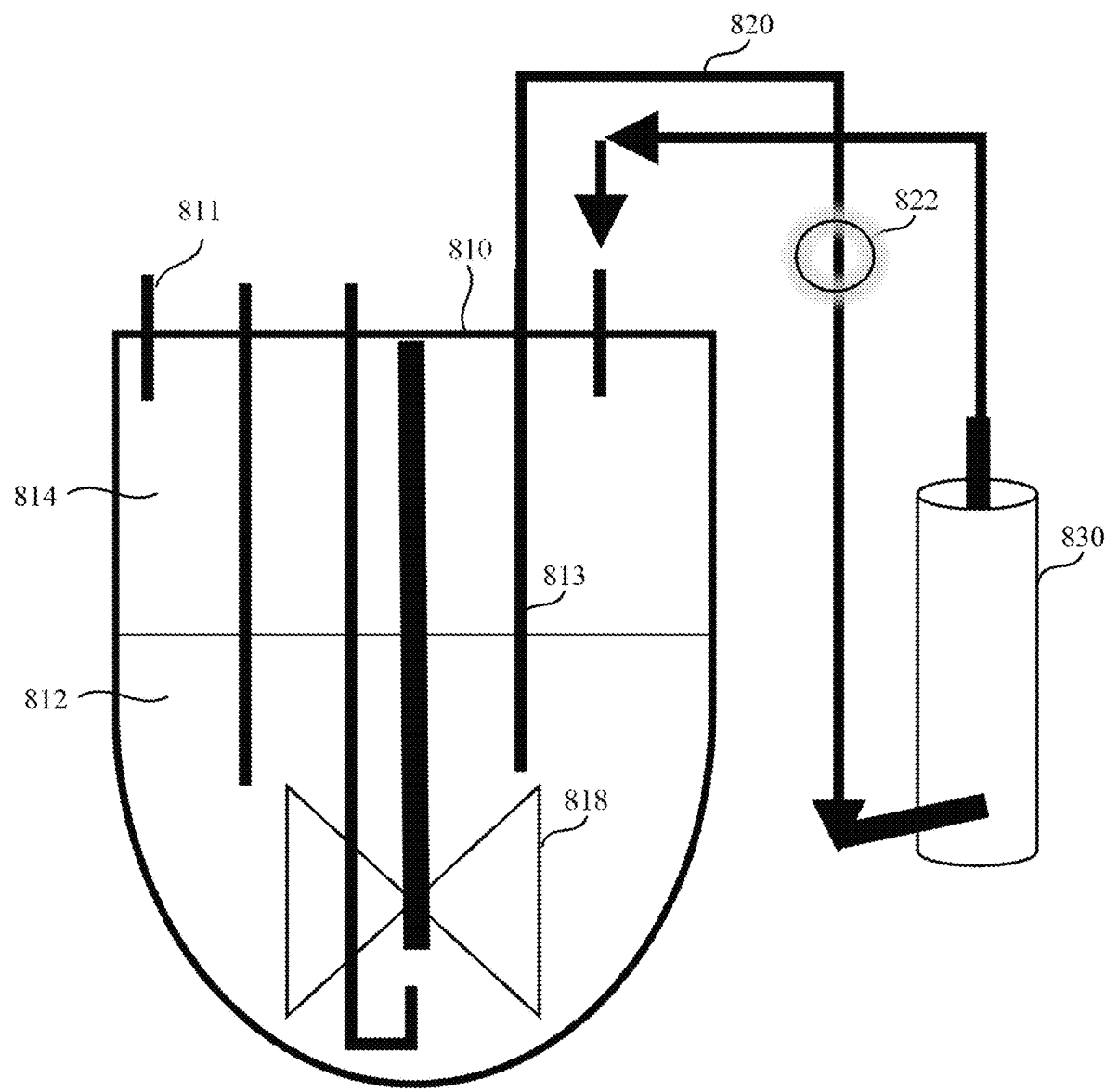
FIG. 8 is a schematic diagram of an illustrative variation of a bioreactor system

In some variations, a method of preparing cell culture media may include moving fluids between a bioreactor and enclosed vessel. FIG. 8 is a schematic diagram of a bioreactor system (800) comprising a bioreactor (810), enclosed vessel (830) (e.g., mixing vessel, vortex chamber), and fluid pump (822). In some variations, the bioreactor (810) may be configured to grow a comestible meat product. The enclosed vessel (830) may be configured to hydrate dehydrated cell culture media. In some variations, the bioreactor (810) and enclosed vessel (830) may be in fluid communication via a set of fluid conduits (820). For example, fluid (812) may be introduced from the bioreactor (810) to the enclosed vessel (830) using pump (822). For example, a vortex flow may be generated in the enclosed vessel (830) using the pump (822) and fluid (812) from the bioreactor (810). The hydrated cell culture media may then be pumped from the enclosed vessel (830) to the bioreactor (810) using the pump (822). In some variations, an agitator (818) may be configured to rotate and stir the cell culture media introduced into the bioreactor (810).

In some variations, a method of preparing cell culture media may include introducing water (e.g., deionized water) into the bioreactor (810) and cell culture media (e.g., dry culture media, dehydrated cell culture media) into the enclosed vessel (830). An agitator (818) may be rotated to stir fluid (812) in the bioreactor (810). In some variations, a fluid conduit (820) may couple the bioreactor (810) to the enclosed vessel (830). For example, the fluid conduit (820) may couple to a port (813) comprising an outlet below a fluid level of the fluid (812). In some variations, the port (813) may be alternately coupled to a fluid source (e.g., sterilant gas generator) and enclosed vessel (830).

In some variations, the pump (822) may be coupled to the fluid conduit (820). In some variations, the pump (822) may be configured to pump fluid (812) into the enclosed vessel (830) at a predetermined rate to generate a vortex flow, as described herein, to hydrate the dry powder media (DPM) disposed therein. In some variations, the bioreactor (810) may be agitated until the DPM is hydrated. The hydrated cell culture media may be drained from the enclosed vessel (830) into the bioreactor (810).

In some variations, the enclosed vessel (830) may be decoupled (e.g., disconnected) from the bioreactor (810). In some variations, one or more additives (e.g., supplements, growth factors, sodium bicarbonate) may be introduced into the bioreactor (810). In some variations, the cell culture media in the bioreactor (810) may be sampled and one or more measurements (e.g., glucose, osmolality) may be performed. In some variations, a temperature of the system (800) may be measured and/or regulated. In some variations, a pH of the system (800) may be measured and/or equilibrated. In some variations, a sample of the cell culture media may be removed for sterile and/or quality testing. In some variations, one or more cells may be introduced into the bioreactor (810) and grown.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

Although the foregoing implementations has, for the purposes of clarity and understanding, been described in some detail by of illustration and example, it will be apparent that certain changes and modifications may be practiced, and are intended to fall within the scope of the appended claims. Additionally, it should be understood that the components and characteristics of the substrates described herein may be used in any combination, and the methods described herein may comprise all or a portion of the elements described herein. The description of certain elements or characteristics with respect to a specific figure are not intended to be limiting or nor should they be interpreted to suggest that the element cannot be used in combination with any of the other described elements.

In addition, any combination of two or more such features, structure, systems, articles, materials, kits, steps and/or methods, disclosed herein, if such features, structure, systems, articles, materials, kits, steps and/or methods are not mutually inconsistent, is included within the inventive scope of the present disclosure. Moreover, some variations disclosed herein may be distinguishable from the prior art for specifically lacking one or more features/elements/functionality found in a reference or combination of references (i.e., claims directed to such variations may include negative limitations).

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

We claim:

1. A method of preparing cell culture media for growing cell-based products, the method comprising:
    sterilizing an enclosed vessel and a hydrated cell culture media disposed therein in preparation to grow mammalian, avian, or aquatic animal cells by:
        circulating a chlorine dioxide gas in the enclosed vessel to sterilize the hydrated cell culture media and the enclosed vessel; and
        agitating the hydrated cell culture media while circulating the chlorine dioxide gas in the enclosed vessel for a dwell time sufficient to sterilize the hydrated cell culture media and the enclosed vessel.

2. The method of claim 1, wherein circulating the chlorine dioxide gas in the enclosed vessel comprises introducing the chlorine dioxide gas into a headspace of the enclosed vessel.

3. The method of claim 2, wherein agitating the hydrated cell culture media comprises generating a vortex flow in the enclosed vessel.

4. The method of claim 1, wherein the enclosed vessel comprises a sealed chamber in fluidic communication with a bioreactor configured to grow a comestible meat product in a sealed environment.

5. The method of claim 4, further comprising introducing the sterilized and hydrated cell culture media into the bioreactor.

6. The method of claim 5, further comprising agitating the sterilized and hydrated cell culture media in the bioreactor while circulating the chlorine dioxide gas in the bioreactor.

7. The method of claim 1, wherein agitating the hydrated cell culture media while circulating the chlorine dioxide gas sterilizes and prepares the hydrated cell culture media for growth of the mammalian, avian, or aquatic animal cells.

8. The method of claim 1, wherein the hydrated cell culture media comprises an incomplete composition configured to grow cells with an addition of at least one other composition.

9. The method of claim 1, wherein the enclosed vessel is a first bioreactor, and further comprising circulating the chlorine dioxide gas from the first bioreactor to a second bioreactor in fluidic communication with the first bioreactor.

10. The method of claim 9, wherein the first bioreactor and the second bioreactor comprise one or more substrates.

11. The method of claim 10, wherein the first bioreactor and the second bioreactor are configured to grow a comestible meat product.

12. The method of claim 1, wherein the chlorine dioxide gas does not leave a residue on either organic or inorganic matter within the enclosed vessel after sterilization.

13. The method of claim 1, further comprising removing the chlorine dioxide gas from the enclosed vessel.

14. The method of claim 13, further comprising generating a sterilization notification after removing the chlorine dioxide gas from the enclosed vessel, wherein the sterilization notification indicates an amount of the chlorine dioxide gas removed from the enclosed vessel.

15. The method of claim 13, further comprising agitating the sterilized and hydrated cell culture media while removing the chlorine dioxide gas from the enclosed vessel.

16. The method of claim 13, further comprising neutralizing the chlorine dioxide gas after removing the chlorine dioxide gas from the enclosed vessel.

17. The method of claim 16, further comprising neutralizing the chlorine dioxide gas utilizing an active carbon scrubber.

18. The method of claim 6, further comprising:
    removing the chlorine dioxide gas from the bioreactor; and
    introducing, in response to removing the chlorine dioxide gas from the bioreactor, an additive to the bioreactor, the additive comprising one or more of an amino acid, an anti-foaming agent, a shear protectant, a protein, a nutrient mixture, mammalian cells, a bacteria, or yeast cells.

19. A method of preparing cell culture media for growing cell-based products, the method comprising:
    sterilizing an enclosed vessel and hydrated cell culture media disposed therein in preparation to grow mammalian, avian, or aquatic animal cells by circulating a chlorine dioxide gas in the enclosed vessel while agitating the hydrated cell culture media for a dwell time sufficient to sterilize the hydrated cell culture media and the enclosed vessel; and
    introducing, in response to sterilizing the enclosed vessel and the hydrated cell culture media disposed therein, an additive into the enclosed vessel to further prepare the hydrated cell culture media to grow the mammalian, avian, or aquatic animal cells.

20. The method of claim 19, wherein the additive comprises one or more of an amino acid, an anti-foaming agent, a shear protectant, a protein, a nutrient mixture, mammalian cells, a bacteria, a yeast cells.

* * * * *